(12) United States Patent
Pasloske et al.

(10) Patent No.: US 6,777,210 B1
(45) Date of Patent: Aug. 17, 2004

(54) METHOD AND REAGENTS FOR INACTIVATING RIBONUCLEASES RNASE A, RNASE I AND RNASE T1

(75) Inventors: Brittan L. Pasloske, Austin, TX (US); William Wu, Austin, TX (US)

(73) Assignee: Ambion, Inc., Austin, TX (US)

( * ) Notice: Subject to any disclaimer, the term of this patent is extended or adjusted under 35 U.S.C. 154(b) by 0 days.

(21) Appl. No.: 09/160,284

(22) Filed: Sep. 24, 1998

(51) Int. Cl.[7] .................................. C12P 19/34

(52) U.S. Cl. .................... 435/91.21; 435/199; 435/270; 536/25.1

(58) Field of Search .................. 536/25.1; 435/199, 435/270, 91.21

(56) References Cited

U.S. PATENT DOCUMENTS

| | | | |
|---|---|---|---|
| 5,552,302 A | * 9/1996 | Lewis et al. | 435/492 |
| 5,677,124 A | 10/1997 | DuBois et al. | 435/5 |
| 5,919,625 A | 7/1999 | DuBois et al. | 435/6 |
| 5,936,262 A | * 8/1999 | Batra et al. | 435/6 |
| 5,939,262 A | 8/1999 | Pasloske et al. | 435/6 |
| 5,945,515 A | * 8/1999 | Chomczynski | 530/412 |
| 6,204,375 B1 | * 3/2001 | Lader | 536/25.4 |

FOREIGN PATENT DOCUMENTS

| | | | |
|---|---|---|---|
| DE | 9607202 | * | 8/1997 |
| EP | 0655505 | * | 5/1995 |
| WO | WO00/17320 A2 | * | 3/2000 |

OTHER PUBLICATIONS

Lehninger, A. L., *Biochemistry, Second Edition,* Worth Publishers, Inc., New York, NY, Jul., 1978; Only pp. 99–102, 226–227 & 945–946 supplied.*

Rüegg et al., "Reductive Cleavage of Cystine Disulfides with Tributylphosphine," etc., Chs. 10–12 in *Methods in Enzymology, 47,* 111–126 (1977).*

Carmack et al., "The Synthesis of the Optically Active Cleland Reagent [(−)−1, 4–Dithio–$L_R$–threitol]," *Journal of Organic Chemistry, 33*(5), 2171–2173 (May, 1968).*

Cleland's Reagent, a reprint of "Cleland, 'Dithiothreitol, a New Protective Reagent for SH Groups,' *Biochemistry, 3*(4), 480–482 (Apr., 1964)" including a bibliography including citations dated up to 1975, Hoechst AG/Calbiochem–Behring, La Jolla CA, document No. 4926–483.*

Khesin et al., "Ribonuclease Activity in Preparation of Human Leukocytic Interferon," *Bulletin of Experimental Biology and Medicine, 82*(7), 997–1000 (1976); EMBASE abstract also supplied.*

Ginsberg et al., "Enzymic Breakdown of Proteins. II. Action of Pepsin on Ribonuclease and Considerations on the Structure of Ribonuclease," *Journal of Biological Chemistry, 235*(1), 115–123 (Jan., 1960).*

Cho et al., "Ribonuclease Inhibitor from Pig Brain: Purification, Characterization, and Direct Spectrophotmetric Assay," *Analytical Biochemistry, 176*(1), 175–179 (Jan., 1989).* van Gemen et al., "A One–Tube Quantitative HIV–1 RNA NASBA Nucleic Acid Amplification Assay Using Electrochemoluminescent (ECL) Labelled Probes," *Journal of Virological Methods, 49*(2), 157–168 (Sep., 1994).*

Mulder et al., "Rapid and Simple PCR Assay for Quantitation of Human Immunodeficiency Virus Type 1 RNA in Plasma: Application to Acute Retroviral Infection," *Journal of Clinical Microbiology, 32*(2), 292–300 (Feb., 1994).*

Pachl et al., "Rapid and Precise Quantification of HIV–1 RNA in Plasma Using a Branched DNA Signal Amplification Assay," *Journal of Acquired Immune Deficiency Syndromes and Human Retrovirology, 8*(5), 446–454 (Apr. 15, 1995).*

Alliaga, et al., "Isolation and characterization of polyribosomes from the salivary glands of rhynchosciara americana," *Cell Differentiation,* 4:243–255, 1975. month of publication data is unavailable for this reference.

Barnard, "Ribonucleases," *Annu. Rev. Biochem.,* 38:677–732, 1969. month of publication data is unavailable for this reference.

Blumberg, "Creating a ribonuclease–free environment," *Methods Enzymol.,* 152:20–24, 1987. month of publication data is unavailable for this reference.

Boshes, "Characterization of two populations by cell fractionation and isotopic labelling the nucleic acid and protein precursors," *J. Cell Biol.,* 46:477–490, 1970. month of publication data is unavailable for this reference.

Cleland, "Dithiothreitol, a new protective reagent for sit groups," *Biochemistry,* 3:480–482, 1964, (Issue No. 4, Apr., 1964).

Chomczynski and Sacchi, "Single step method of rna isolation by acid guanidine isothiocyanate–phenol–chloroform extraction," *Anal. Biochem.,* 162:156–159, 1987. month of publication data is unavailable for this reference.

(List continued on next page.)

*Primary Examiner*—James O. Wilson
*Assistant Examiner*—L E Crane
(74) *Attorney, Agent, or Firm*—Fulbright & Jaworski L.L.P.

(57) ABSTRACT

The present invention is a general method for irreversibly inactivating ribonucleases. Ribonucleases are completely inactivated by treating them with a reducing agent and heat. RNA samples contaminated with ribonuclease may be treated with this method to protect them from degradation. The RNA may then be used directly in a variety of enzymatic reactions and molecular biology techniques. This method may also be applied to a variety of molecular biology reagents which may be contaminated with ribonuclease to protect an RNA from being degraded when incubated with the reagent.

38 Claims, 3 Drawing Sheets

OTHER PUBLICATIONS

Chomczynski, "Solubolization in formamide protects rna from degradation", *Nucleic Acids Res.,* 20:3791, 1992. (Issue No. 14). month of publication data is unavailable for this reference.

Dickman, "Activation and inhibition of beef pancreas ribonuclease," *Biochemica et Biophysica Acta,* 21:539–545, 1956. month of publication data is unavailable for this reference.

Dickman and Ring, "Effects of ionic strength on ribonucleic acid structure and ribonuclease activity," *J. Biol. Chem.,* 231:741–750, 1958. (Issue No. 2). month of publication data is unavailable for this reference.

Eftink and Biltonen, "Energetics of ribonuclease a catalysis 1, ph, ionic strength, and solvent isotope dependence of the hydrolysis of cytidine cyclic 2',3'–phosphate," *Biochemistry,* 22:5123–5134, 1983. (Issue No. 22). month of publication data is unavailable for this reference.

Hummel and Anderson, "Ribonuclease adsorption on glass surfaces," *Arch. Biochem. Biophys.,* 112:443–447, 1965. month of publication data is unavailable for this reference.

Kalnitsky et al., "Some factors which affect the enzymatic digestion of ribonucleic acid," *J. Biol. Chem.,* 234:1512–1516, 1959. (Issue No. 6, Jun., 1959).

Jacoli and Ronald, "Inhibition of ribonuclease activity by bentonite," *Can. J. Biochem.,* 51: 1558–1565, 1973. month of publication data is unavailable for this reference.

Jones, "On the efficacy of commonly used ribonuclease inhibitors," *Biochem. and Biophys. Res. Comm.,* 69:469–474, 1976. (Issue No. 2). month of publication data is unavailable for this reference.

Lin, "Inactivation of pancreatic ribonuclease with hydroxylamine–oxygen–curric ion," *Biochimica et Biophysica Acta,* 263:680–682, 1972. month of publication data is unavailable for this reference.

McGeehan and Benner, "An improved system for expressing pancreatic ribonuclease in *Eshcerichia coli*," *FEBS Lett.,* 247:55–56, 1989. (Issue No. 1, Apr., 1989).

Mendelsohn and Young, "Efficacy of sodium dodecyl sulfate, diethyl pyrocarbonate, proteinase k and heparin using a sensitive ribonuclease assay," *Biochimica et Biophysica Acta,* 519:461–473, 1978. month of publication data is unavailable for this reference.

Murphy et al., "A potent, cost–effective rnase inhibitor", *Biotechniques,* 18:1068–1073, 1995. (Iss. No. 6 , month of publication data is unavailable for this reference.

Murthy and Sirdeshmukh, "Sensitivity of monomeric and dimeric forms of bovine seminal ribonuclease to human placental ribonuclease inhibitor," *Biochem. J.,* 281:343–348, 1992.

Rothwarf and Scheraga, "Regeneration and reduction of native bovine pancreatic ribonuclease a with oxidized and reduced dithiorthreitol," *J. Am. Chem. Soc.,* 113:6293–6294, 1991. month of publication data is unavailable for this reference.

Ryle and Amfinsen, "Studies on the disulfide bridges in ribonuclease," *Biochimica et Biophysica Acta,* 24:633–635, 1957. month of publication data is unavailable for this reference.

Spackman et al., "The disulfide bonds of ribonuclease," *J. Biol. Chem.,* 235: 648–659, 1960. (#3, 3/60).

Wiener et al., "Inhibition of ribonuclease by diethyl pyrocarbonate and other methods," *Biochimica et Biophysica Acta,* 259:378–385, 1972. month of publication data is unavailable for this reference.

Wolf et al., "A mechanism of the irreversible inactivation of bovine pancreatic ribonuclease by diethylpyrocarbonate," *Eur. J. Biochem.,* 13:519–525, 1970. (Issue No. 3). month of publication data is unavailable for this reference.

Volkin and Klibanov, "Thermal destruction processes in proteins involving cystine residues," *J. Biol. Chem.,* 262:2945–2950, 1987. (Issue No. 7, Mar. 5, 1987).

Zahler and Cleland, "A specific and sensitive assay for disulfides," *J. Biol. Chem.,* 243:716–719, 1968. (Issue No 4, Feb. 25, 1968).

Zale and Klibanov, "Why does ribonuclease irreversibly inactivated at high temperature?," *Biochemistry,* 25:5432–5444, 1986. (Issue No. 19). month of publication data is unavailable for this reference.

\* cited by examiner

METHOD AND REAGENTS FOR INACTIVATING RIBONUCLEASES RNASE A, RNASE I AND RNASE T1

BACKGROUND OF THE INVENTION

1. Field of the Invention

The present invention relates generally to the field of molecular biology. More particularly, it concerns the inactivation of ribonucleases (RNases) which can degrade RNA.

2. Description of Related Art

The quality of an RNA preparation greatly affects the results obtained when analyzing it by a number of different molecular biology techniques such as northern blotting, ribonuclease protection assays and RT-PCR (Reverse Transcriptase-Polymerase Chain Reaction). Degraded RNA will produce a lower signal than in an equivalent intact RNA sample.

RNA is much more susceptible to degradation than DNA (Sambrook et al., 1989). RNA is readily hydrolyzed when exposed to conditions of high pH, metal cations, high temperatures and contaminating ribonucleases. A major cause of RNA degradation is ribonuclease contamination, and this must be guarded against in virtually all RNA-related procedures, including RNA isolation, mRNA purification, RNA storage, northern blotting, nuclease protection assays, RT-PCR, in vitro transcription and/or translation and RNA diagnostics. In addition to the endogenous ribonucleases from cells and tissues, finger grease and bacteria and/or fungi in airborne dust particles are common sources of ribonuclease. To minimize ribonuclease contamination, appropriate precautions must be followed when handling RNA (Blumberg, 1987; Wu, 1997).

Ribonucleases are difficult to inactivate. For example, while at 90° C., bovine pancreatic ribonuclease A (RNase A) has no activity. However, if the enzyme is quickly cooled to 25° C., the activity is fully restored. This process is known as reversible thermal denaturation. If the RNase A is incubated at 90° C. over time, then decreasing fractions of the activity are recovered at 25° C. This process is known as irreversible thermoinactivation. At 90° C., it takes several hours to inactivate RNase A (Zale and Klibanov, 1986). Much of the lost activity is attributed to disulfide interchange (Zale and Klibanov, 1986). Further, the inventors and others have found that ribonucleases can even withstand autoclaving (121° C., 15 psi, 15 minutes) to some degree. Spackman et al. (1960) tested the stability of RNase A and concluded that it was stable to heat, extremes of pH, and the protein denaturant, urea, results emphasizing the difficulty researchers have had inactivating ribonucleases. For the above reason, a variety of methods other than heating have been developed to inhibit or inactivate ribonucleases. These methods, and their disadvantages, are described below.

In one method of destroying RNases, diethyl pyrocarbonate (DEPC) is added to final concentration of 0.1% to molecular biology reagents, glassware or electrophoresis apparatus, followed by incubating at 37° C. for several hours and then autoclaving for 15–20 minutes to destroy the DEPC (Wolf et al., 1970). DEPC reacts with the ε-amino groups of lysine and the carboxylic groups of aspartate and glutamate both intra- and intermolecularly (Wolf et al., 1970). This chemical reaction forms polymers of the ribonuclease. However, there are several disadvantages to using DEPC: (1) It is a possible carcinogen and is hazardous to humans; (2) some commonly used molecular biology reagents such as Tris react with and inactivate DEPC; (3) treatment of samples with DEPC is time-consuming; (4) DEPC reacts with the adenine residues of RNA, rendering it inactive in in vitro translation reactions (Blumberg, 1987) and 5) If all of the DEPC is not destroyed by autoclaving, remaining trace amounts may inhibit subsequent enzymatic reactions.

Traditionally, RNA is stored in DEPC-treated water or TE buffer. However, the RNA is not protected from degradation if the sample or the storage solution has a minor ribonuclease contamination. It has been suggested that RNA be stored in ethanol or formamide to protect an RNA sample from degradation because these environments minimize ribonuclease activity (Chomczynski, 1992). The obvious disadvantage is that the RNA sample cannot be directly utilized for analysis or enzymatic reactions unless the ethanol or formamide is removed.

Guanidinium thiocyanate is commonly used to inhibit RNases during RNA isolation (Chomczynski and Sacchi, 1987; Sambrook et al., 1989). A high concentration of guanidinium thiocyanate combined with β-mercaptoethanol is used to isolate RNA from tissues, even those that are rich in ribonucleases, such as pancreas (Chirgwin et al., 1979). Guanidinium is an effective inhibitor of most enzymes due to its chaotropic nature. However, if RNA is dissolved in guanidinium, then it must first be purified from the guanidinium prior to being used in an enzymatic reaction.

Vanadyl-ribonucleoside complexes (VRC) may be used to inhibit RNases during RNA preparation (Berger and Birkenmeier, 1979). The drawback to using VRC, is that VRC strongly inhibits the translation of mRNA in cell-free systems and must be removed from RNA samples by phenol extraction (Sambrook et al., 1989).

Favaloro et al. (1980) employed macaloid, a clay, to absorb RNases. A limitation of this method is that it is difficult to completely remove the clay from RNA samples. Other reagents have been used to inhibit ribonucleases including SDS, EDTA, proteinase K, heparin, hydroxylamine-oxygen-cupric ion, bentonite and ammonium sulfate (Allewell and Sama, 1974; Jocoli and Ronald, 1973; Lin, 1972; Jones, 1976; Mendelsohn and Young, 1978). None of these reagents are strong inhibitors alone, although their inhibitory effect may be improved by using them in combination. Like many of the RNase inhibitors already described, although these chemicals inhibit RNase activity, they also may inhibit other enzymes such as reverse transcriptase and DNase I. Therefore, the RNA must be purified away from the inhibitory reagent(s) before it can be subjected to other enzymatic processes.

Two types of proteinaceous RNase inhibitors are commercially available: human placental ribonuclease inhibitor (Blackburn et al., 1977) and PRIME Inhibitor™ (Murphy et al., 1995). RNases of the class A family bind tightly to these protein inhibitors and form noncovalent complexes that are enzymatically inactive. The major disadvantage of these inhibitors is that they have a narrow spectrum of specificity. They do not inhibit other classes of RNases. Another disadvantage when using placental ribonuclease inhibitor is that it denatures within hours at 37° C., releasing the bound ribonuclease. Thus, the RNA sample is only protected for only a few hours at most.

Reducing agents are frequently used as adjuvants to RNA isolation solutions in conjunction with denaturants to reduce the disulfide bonds in RNases that are rendered accessible by the denaturant. Commonly used reducing reagents are β-mercaptoethanol, dithiothreitol (DTT), dithioerythritol (DTE), and glutathione. Another such reducing agent is the amino acid cysteine. β-mercaptoethanol is often included in RNA isolation solutions combined with guanidinium thiocyanate to reduce ribonuclease activity and solubolize proteins (Chomcyznski and Sacchi, 1987). DTT is the strongest reducing reagent of the three listed.

DTT has low redox potential (−0.33 volts at pH 7.0) and is capable of maintaining monothiols effectively in the reduced form and of reducing disulfides quantitatively (Cleland, 1964). DTT acts as a protective agent for free sulfhydryl groups. It is highly water soluble, with little tendency to be oxidized directly by air, and is superior to other thiols used as protective reagents. DTT's reducing activity can be accurately assayed using 5, 5'-dithiobis (2-nitrobenzoic acid) or DTNB (Cleland, 1964). The reduction of DTNB mediated by DTT generates a yellow color whose absorbance can be measured at 412 nm using a spectrophotometer. RNase A, RNase 1 and RNase T1 all contain disulfide bonds (Ryle and Anfinesen, 1957; Barnard, 1969) and, therefore, are susceptible to reduction.

DTT has been used as an inhibitor of RNase A in the isolation of polyribosomes (Boshes, 1970; Aliaga, 1975). In Boshes' experiment, polyribosome preparations were treated with RNase A (10 μg/ml) in solution A (10 mM $MgCl_2$: 10 mM Tris [pH 7.6 ]: 50 mM KCl) in the presence or absence of 4 mM DTT at 4° C. for 20 minutes. The treatment of polyribosomes with RNase A generated monoribosomes. Boshes observed that polyribosomes treated with RNase A in the presence of 4 mM DTT reduced the conversion of polyribosomes to monoribosomes and from that result he concluded that DTT was an RNase inhibitor. Boshes' statement was based on the effect of DTT on the conversion of polyribosomes to monoribosomes by RNase A. He did not directly assay the degradation of purified RNA. Since Boshes was working with a complex, uncharacterized protein mixture, it is unclear as to what may have been responsible for the decreased production of monoribosomes. For example, the addition of DTT may have increased the activity of the endogenous mammalian RNase inhibitors rather than act directly on the RNases. These RNase inhibitors require a reducing environment for activity.

Heat has been used to inactivate RNase A by mediating the breakage of disulfide bonds. Zale and Klibanov (1986) performed inactivation of RNase A at 90° C. and pH 6.0 for 1 hour, which induced the following chemical changes: disulfide interchange, β-elimination of cysteine residues, and deamidation of asparagine. This type of heat treatment did not completely inactivate the ribonuclease. A major disadvantage is that a long-term, high-temperature treatment (90–100° C.) is incompatible with RNA. Such treatment promotes the hydrolysis of RNA. In fact, the inventors have found that total RNA incubated at 65° C. for several hours is almost completely degraded. Thus, treating an RNase sample with extreme heat to inactivate ribonucleases will mediate the distruction of the RNA which the user is trying to protect.

SUMMARY OF THE INVENTION

The present invention provides a general method for rapidly inactivating ribonucleases and RNA storage solutions adapted for use in such methods. These methods comprise the steps of obtaining a sample; obtaining a reducing agent; admixing the reducing reagent and sample; and heating.

The inventors' method for inactivating ribonuclease can protect RNA from ribonuclease degradation during storage. More importantly, the RNA samples can be used immediately after ribonuclease inactivation for RNA analysis, and in enzymatic reactions such as the synthesis of cDNA by reverse transcriptase and the degradation cellular DNA by DNase I.

As used herein, the terms "RNase inactivation" or the "inactivation of RNases" denotes that there is no detectable degradation of the sample RNA under the assay conditions used.

In one embodiment, the present invention relates to reagents for use in methods for inactivating ribonucleases and such methods comprising: (a) obtaining a sample; (b) obtaining a reducing agent; (c) admixing the sample and the reducing agent; and (d) heating the admixture, wherein ribonucleases in the sample are inactivated. There are many different manners in which the methods and reagents of the present invention may be used. However, in a preferred embodiment, the reagents and methods will be used to inactivate any ribonucleases that are present in a sample that is a reagent used in molecular biology, either in cases where ribonuclease contamination is known or expected to have occurred, or simply as an additional prophylactic step in attempts to avoid RNase contamination. As discussed above, ribonuclease contamination can seriously affect the results of molecular biological assays. Therefore, there is great value in having simple, efficient methods for preventing ribonuclease contamination of molecular biology reagents. In many cases, the molecular biology reagent will be one employed in the handling of RNA, water, TE buffer, 20×SSC, 10×MOPS, Tris buffer, EDTA, nucleic acid hybridization buffer, sodium acetate buffer, formalin tissue fixative, in situ hybridization buffer, or nucleic acid storage buffer/ solution.

Any agents and reagents having reducing properties are well known to those of skill in the art, and, by employing assays described herein, one of ordinary skill in the art will be able to determine which of any of these reducing agents will be of use in the present invention. Presently preferred reducing agents are those comprising DTT, β-mercaptoethanol, cysteine, or dithioerithritol. The final concentration of these reducing agents in the solution that is to be protected from ribonuclease can be any which functions to achieve the ribonuclease protective activity that is the purpose of the invention. Presently preferred concentrations are those between 0.5 and 500 mM reducing agent in the admixture of the sample and the reducing agent. More presently preferred concentrations are between 1 and 200 mM in the admixture. Even more presently preferred concentrations are between 2 and 60 mM. The presently most preferred concentration is 20 mM in the admixture. Of course, the invention is in no way limited to these preferred concentrations.

In most cases, the reducing agent is comprised in a buffer solution prior to admixing. The buffer solution will comprise the agent at a high enough concentration such that the final concentration of the agent in the admixture is sufficient to realize the ribonuclease protective goals of the invention. The buffer solution may also comprise a chelator such as sodium citrate, EGTA, or EDTA.

The admixture may be heated to any temperature and for any amount of time that is sufficient to accomplish the ribonuclease inactivation goals of the invention. Presently preferred conditions call of the heating of the admixture to at least 37° C. for at least 4 minutes The heating may be accomplished by any means standardly employed in a biological lab. The inventors typically use a heat block or water bath that has been set to the desired temperature.

One of the advantages of the present invention is that the methods do not affect the stability of any RNA that is comprised in the solution that is being treated to inactivate ribonucleases. Therefore, a specific embodiment of the invention comprises methods for inactivating ribonucleases in the presence of RNA comprising: (a) obtaining an RNA sample; (b) obtaining a reducing agent; (c) admixing the sample and the reducing agent; and (d) heating the admixture, wherein ribonucleases in the sample are inactivated. The RNA sample may be any sample that contains RNA, including but not limited to a tissue sample, a cell sample, a crude cell preparation, isolated total RNA, and any form of purified RNA. In a preferred embodiment, the sample is comprised of purified RNA. The reducing agents, other components, concentrations, times, and temperatures are typically as described above.

In some embodiments, the invention relates to methods for sequential inactivation of any ribonucleases in a sample such that any ribonucleases introduced to the sample at some time after a first inactivation procedure may be inactivated comprising: a) obtaining a sample; b) obtaining a reducing agent; c) admixing the sample and the reducing agent; d) performing a first heating of the admixture, whereby any ribonucleases in the admixture are inactivated; e) determining that a further inactivation procedure is warranted to inactivate any ribonucleases that may have been introduced to the sample subsequent to the first heating; f) performing a second heating of the admixture, whereby ribonucleases in the admixture are inactivated. The benefits of these methods are clear. One may have a sample of RNA that also contains an appropriate amount of reducing agent. Prior to storage of the RNA, one can simply heat the sample for an appropriate length of time to an appropriate temperature, thereby inactivating any ribonucleases. The next time the RNA is accessed, the remaining RNA may be reheated to inactivate any ribonucleases that might have been introduced into the sample by the access procedure. This process may be carried out an indefinite number of times throughout the storage life of the RNA.

The present invention also comprises solutions for storing RNA comprising: a) a reducing agent; and b) an RNA sample. In some preferred embodiments, the reducing agent will be selected from the group consisting of DTT, dithioeritol, β-mercaptoethatnol, and cysteine. The final concentration of the reducing agent in the solution can be any which functions to achieve the ribonuclease protective activity that is the purpose of the invention upon heating. Presently preferred concentration are those between 0.5 and 500 mM reducing agent in the solution. More presently preferred concentrations are between 1 and 200 mM in the solution. Even more presently preferred concentrations are between 2 and 60 mM. The presently most preferred concentration is 20 mM in the solution. Of course, the invention is in no way limited to these preferred concentrations. Some preferred RNA storage solution comprise a buffer, and presently preferred pHs of the solution are between 5.0–7.0. High pHs mediate the hydrolysis of RNA. However, any pH that does not adversely affect the RNA may be used. The solution may also comprise a metal chelator such as, for example, sodium citrate, EGTA, or EDTA. The chelator is sometimes desired because some metal cations can mediate the hydrolysis of RNA in a sample.

Following long-standing patent law, the words "a" and "an," when used in conjunction with the word "comprising" in the claims or specification, denotes one or more.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
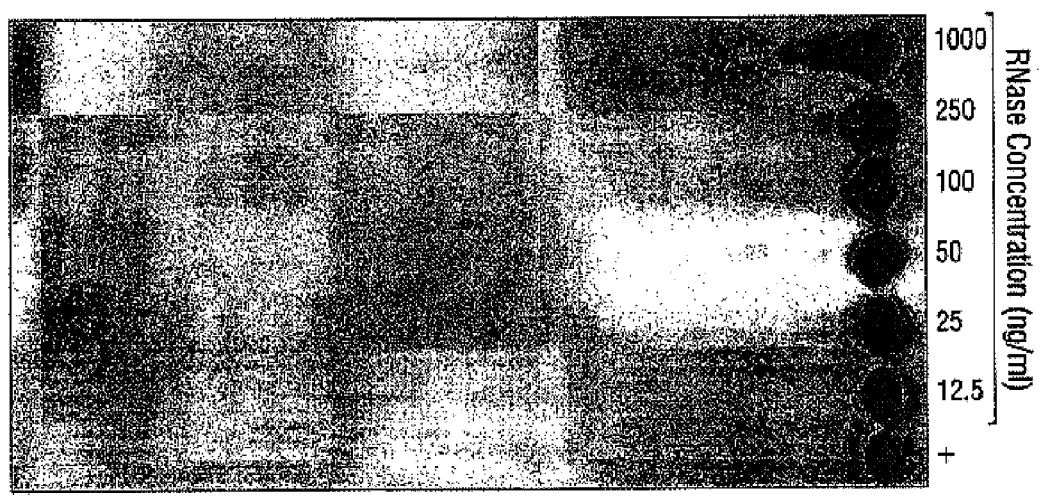
FIG. 1. DTT-heat inactivation of different RNase concentrations. The RNase mixture was made to different concentrations in 20 mM DTT: 1 mM sodium citrate (pH 6.4). The RNase samples were incubated at 60° C. for 20 minutes. A radioactive RNA probe was added to the treated RNase samples, incubated at 37° C. for 16 hours, fractionated in a denaturing 5% acrylamide gel and exposed to x-ray film. The (+) lane is the RNA probe which did not contain DTT or RNase but was incubated at 37° C. for 16 hours.

The present invention relates to methods for inactivating ribonucleases, which employ at least one reducing reagent and heat of at least 37° C. Generally, the reducing agent is added to buffers, solutions or water containing a potential RNase contamination. RNases are then inactivated by heating. The preferred reducing reagents are DTT, DTE, cysteine, and β-mercaptoethanol. To effectively inactivate RNases, the presently preferred method is to add DTT to a final concentration of 20 mM to the sample and then incubate at 60° C. for 8 minutes. The following examples provide detailed description and utilities of the present invention.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Criteria for the Analysis of Ribonuclease Inactivation

The inventors routinely perform assays on RNA designed to assess RNase activity in a sample. Two different assays are typically used for the detection of ribonuclease activity, non-isotopic and isotopic. Each assay generates similar data with regard to the sensitivity of detection. In both assays, the inactivation process is typically performed on a mixture of three different ribonucleases: RNase A, RNase 1, and RNase T1. Each ribonuclease is purified from a different species: human, *E. coli* and a fungus, respectively. The three RNases are very different from each other in their origin, substrate specificity and protein sequence. In this way, the inactivation process can test three completely different but well characterized ribonucleases. The standard stock RNase mixture employed in the following examples is prepared by combining 1 μl RNase 1 (100 U/μl; Ambion), 1 μl RNase cocktail (RNase A, 0.5 U/μl; RNase T1, 20 U/μl, Ambion) and 98 μl water.

By employing one or both of these assays, one of skill will be able to determine additional reducing agents that function in the invention. In order to do so, one need only obtain a putative reducing agent that is expected to have RNase inactivating activity and then perform the types of assays performed herein with regard to DTT, cysteine, etc. to determine the utility of the putative reducing agent in the methods and compositions of the invention.

1. Non-Isotopic RNase Inactivation Assay

The non-isotopic assay uses total RNA isolated from mouse as the substrate for the RNase mixture. The assays reported in the following examples were typically performed in a final volume of 10 μl. A quantity of 4 μg of total RNA isolated from mouse liver or brain was dissolved in an aqueous solution, usually water or 1 mM sodium citrate (pH 6.6). The treated ribonuclease sample was added to the total RNA and then incubated at 37° C. for 1 or 16 hours, depending on the sensitivity desired for the assay. After incubation, the RNA was fractionated in a formaldehyde 1% agarose gel. The RNA was detected by staining with ethidium bromide and then illuminating the gel with ultraviolet light. The RNA fluoresces in the gel. Untreated total RNA was also fractionated as a control with the test samples for comparative purposes. Test samples containing inactivated RNase produced the same ethidium bromide staining pattern as the untreated RNA control. Intact total RNA has two major bands produced by the 28S and 18S ribosomal RNA. If the intensities of the ribosomal RNAs became diminished compared to the control RNA, then the RNases were not inactivated by the inactivation treatment. An example of the non-isotopic assay in use in found in Example 6 and the Figure cited therein.

2. Isotopic RNase Inactivation Assay

The isotopic RNase assay uses a radioactive RNA synthesized by in vitro transcription as the RNA substrate. The RNA used in the following examples was 1.9 or 4.0 kb in length. The radioactive RNA was synthesized using a T7 MEGAscript™ transcription kit (Ambion, Inc.). The in vitro transcription reaction mixture contained 1.0 μg of linearized DNA template, 2 μl of 10×transcription buffer, 1 μl of UTP[$\alpha^{32}$P] (800 Ci/mmol), 2 μl of each 75 mM ribonucleotide and 2 μl of the T7 RNA polymerase mix, final volume of 20 μl. The reaction was incubated at 37° C. for 3 hours. The transcript was precipitated with 7.5 M LiCl and resuspended in 0.1 ml of 1 mM sodium citrate (pH 6.6) or RNase free water.

2 μl of the RNA probe was incubated with the test sample in a final volume of 10 μl for about 16 hours at 37° C. After incubation, the RNA was fractionated in a denaturing 6 M urea 5% acrylamide gel and then the gel was exposed to x-ray film. Untreated RNA was also fractionated as a control with the test samples for comparative purposes. Test samples containing no detectable RNase activity produced the same single band as the untreated control RNA. RNase activity was indicated by the intensity of the RNA decreasing and by the appearance of smearing below the intact RNA. An example of the isotopic assay in use is found in Example 3 and the Figure cited therein.

EXAMPLE 2

Boshes' Method does not Inactivate RNases

Boshes (1970) stated that DTT is an RNase inhibitor, a statement based on the observation that the addition of DTT decreased the generation, by RNase A, of polyribosomes to monoribosomes in a crude polyribosome preparation. RNase A (10 μg/ml) activity was inhibited by the addition of 4 mM DTT at 4° C. for 20 minutes (Boshes, 1970). The inventors demonstrated that these conditions are insufficient to inactivate RNase using their assay system. RNase A, at 200 ng/ml instead of 10 μg/ml, was treated with or without 4 mM DTT in Boshes' solution A at 4° C. for 20 minutes. RNase A activity was then tested by incubating mouse liver total RNA with the treated RNase A at 37° C. for 60 minutes. The mouse RNA was then fractionated by electrophoresis in a 1% agarose formaldehyde gel. RNase A at 200 ng/ml was not inactivated using the conditions set forth by Boshes (1970). In fact, the RNA was completely digested. In contrast, the RNase A treated at 60° C. for 20 minutes in the presence of 20 mM DTT was completely inactivated, i.e., the mouse total RNA remained completely intact.

A likely explanation for the observed results is that Boshes used a crude, uncharacterized sample containing a complex set of proteins associated with the polyribosomal fraction. Mammalian RNase inhibitor is found in many tissues and is dependent on reducing conditions for activity. RNase inhibitor binds to RNase to inhibit its activity. Under oxidizing conditions, the RNase inhibitor releases active RNase. Thus when Boshes added DTT to his preparation, he may have restored or increased the activity of the naturally occurring RNase inhibitor.

EXAMPLE 3

Use of Reducing Agents Coupled with Heat Inactivate Ribonucleases

1. Concentrations of RNase Mixture Inactivated by Treating with a Reducing Reagent and Heat.

The RNase mixture was added to 1 mM sodium citrate (pH 6.4) containing 20 mM DTT up to final concentration of 1 μg/ml and incubated at 60° C. for 20 minutes RNase activity was tested using the non-isotopic (1 hour incubation) and the isotopic assays (FIG. 1). As measured by both assays, the RNase mixture was completely inactivated up to 200 ng/ml.

In related experiments, β-mercaptoethanol and DTE at 20 mM were incubated with the RNase mixture at 200 ng/ml at 60° C. for 20 minutes. These reducing reagents had the same effect as DTT in that they were able to inactivate RNase activity completely as measured using the non-isotopic assay.

2. Inactivating RNases in the Presence of RNA

The RNase mixture was added at final concentrations of 200, 100, 50, 25, 12.5, 6.25, 3.125, 1.56, 0.78 and 0.39 ng/ml to mouse liver total RNA (4 μg/10 μl) in 1 mM sodium citrate (pH 6.4): 20 mM DTT. The samples were incubated at 60° C. for 20 minutes and then assessed for RNase activity using the non-isotopic assay, incubating 37° C. for 1 hour. This method of RNase inactivation was able to completely inactivate the RNase mixture up to 3.125 ng/ml in the presence of RNA. It was difficult to test the inactivation process on the higher concentrations of the RNase mixture in the presence of RNA, because the RNA was being degraded by the high concentrations of RNase before the sample could be subjected to the heating step.

EXAMPLE 4

RNase Inactivation is Dependent on DTT Concentration and Temperature

1. Inactivation of the RNase Mixture

To determine the effective temperature and DTT concentration for ribonuclease inactivation, RNase mixtures were prepared to final concentrations of 954, 191, 95, and 64 ng/ml. DTT was added to final concentrations of 5, 10, and 20 mM. The solutions were incubated at 37° C. or 60° C. for 20 minutes. RNase activity was tested using the non-isotopic assay. Higher DTT concentrations and higher temperatures were most effective at inactivating the RNase mixture (Table 1). The RNase mixture at 954 ng/ml could be inactivated by incubating in 20 mM DTT at 60° C. for 20 minutes. Even an RNase mixture at 64 ng/ml could be inactivated by incubating at 37° C. for 20 minutes with 10 mM DTT. The inactivation treatments were equally effective in water, in buffer A [1 mM sodium citrate (pH 6.4)], in buffer B [50 mM Tris-HCl (pH 7.0)] or in buffer C [30 mM NaCl: 3 mM sodium citrate (pH 7.5)].

TABLE 1

RNase Inactivation is Dependent on the DTT Concentration and the Temperature in Water or Different Buffers*

| RNase Mix (ng/ml) | DTT (mM) | RNase Inactivation | | | | Temp. (° C.) |
| --- | --- | --- | --- | --- | --- | --- |
| | | Water | Buffer A | Buffer B | Buffer C | |
| 954 | 5 | − | − | − | − | 60 |
| 191 | 5 | − | − | − | − | 60 |
| 95 | 5 | − | − | − | − | 60 |
| 64 | 5 | + | + | + | + | 60 |
| 954 | 10 | − | − | − | − | 37 |
| 191 | 10 | − | − | − | − | 37 |
| 95 | 10 | − | − | − | − | 37 |
| 64 | 10 | + | + | + | + | 37 |
| 954 | 10 | − | − | − | − | 60 |
| 191 | 10 | + | + | + | + | 60 |
| 95 | 10 | + | + | + | + | 60 |
| 64 | 10 | + | + | + | + | 60 |
| 954 | 20 | + | + | + | + | 60 |
| 191 | 20 | + | + | + | + | 60 |

* 1 mM sodium citrate (pH 6.4), Buffer A; 50 mM Tris-HCl pH 7.0), Buffer B; 30 mM NaCl; 3 mM sodium citrate pH 7.5), Buffer C.
(+) indicates that the RNase mixture was inactivated and (−) indicates that the RNase mixture was not activated as determined by the non-isotopic assay.
The RNase cocktail was made to various concentrations in different buffers in different DTT concentrations and incubated at 37° C. or 60° C. for 20 minutes. Total mouse RNA was added to the treated RNase mixture and incubated at 37° C. for one hour, fractionated in a formaldehyde denaturing 1% agarose gel and the RNA visualized by ethidium bromide staining and UV fluorescence.

2. Heating is Required for Ribonuclease Inactivation

RNase A was diluted to 154 ng/ml in 1 mM sodium citrate (pH 6.4) or in Boshes' (1970) buffer A. DTT was added to the samples to 4 mM or 20 mM and then incubated at 4° C. or 60° C. for 20 minutes. The RNase A was not inactivated by 4 mM or 20 mM DTT at 4° C. for 20 minutes. The mouse total RNA was completely degraded. However, the ribonuclease activity was completely inactivated with 4 mM or 20 mM DTT coupled with heat at 60° C. for 20 minutes. Therefore, the heating step was important for inactivation in this study.

EXAMPLE 5

DTT, DTE and β-mercaptoethanol do not Inhibit Enzymatic Reactions in the Presence of RNA 1. DTT, DTE and β-mercaptoethanol do not Inhibit In Vitro Transcription or Reverse Transcription Reactions.

DTT, DTE and β-mercaptoethanol at 20 mM in standard in vitro transcription reactions or standard reverse transcription (RT) reactions do not inhibit the efficiency of either of these reactions.

Figure 2:
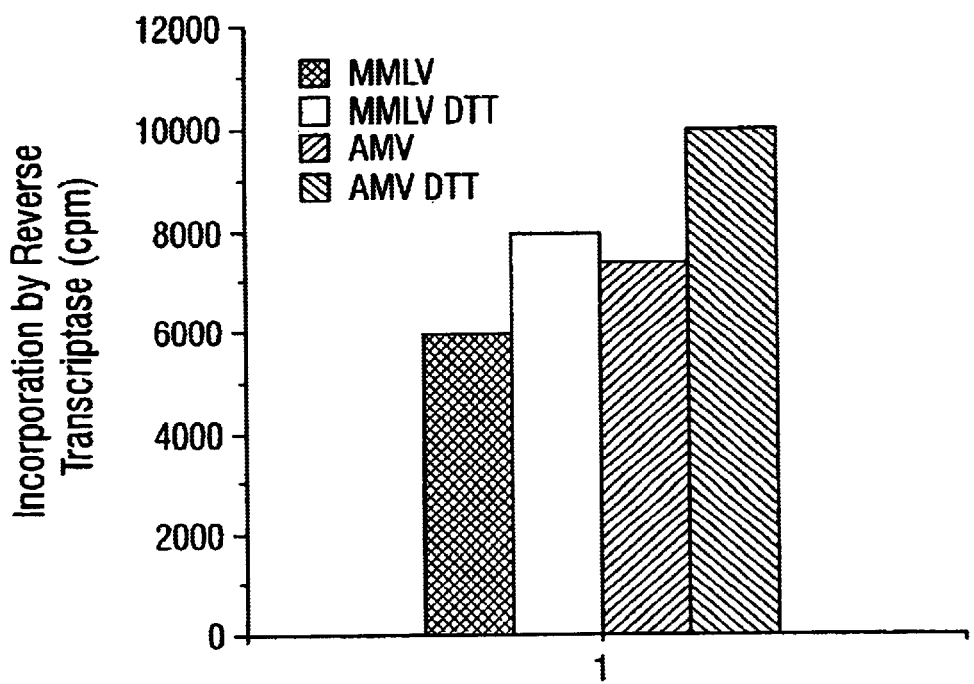
FIG. 2. DTT does not inhibit the AMV or MMLV reverse transcriptases. Reverse transcriptions were performed using the RETROscript™ kit (Ambion, Inc.). Mouse total RNA in DEPC-treated water was reverse transcribed with either MMLV or AMV reverse transcriptase in the presence or absence of 20 mM DTT. dCTP[$\alpha^{32}$P] was included in the reactions to measure the efficiency of reverse transcription. Following incubation at 42° C. for 1 h, 5 μl of each reaction was subjected to TCA precipitation to measure the amount of dCTP[$\alpha^{32}$P] incorporated into cDNA by reverse transcription.

The reverse transcription reactions were performed using the RETROscript™ kit (Ambion, Inc.). The following were assembled with or without 20 mM of the reducing reagents in a final volume of 19 μl: dNTPs (0.5 mM each), oligo dT (5 μM), 0.4 μl dCTP[α-$^{32}$P] (3000 Ci/mmol), 10 mM Tris-HCl (pH 8.3): 50 mM KCl: 1.5 mM MgCl$_2$, mouse brain total RNA (4 μg). The reaction mixtures were incubated at 65° C. for 10 minutes. 1 μl (100 units) of AMV or MMLV reverse transcriptase were added and then the reactions were incubated at 42° C. for 1 hour. Reverse transcription by either enzyme was not inhibited by DTT (FIG. 2) or by DTE or β-mercaptoethanol.

Figure 3:
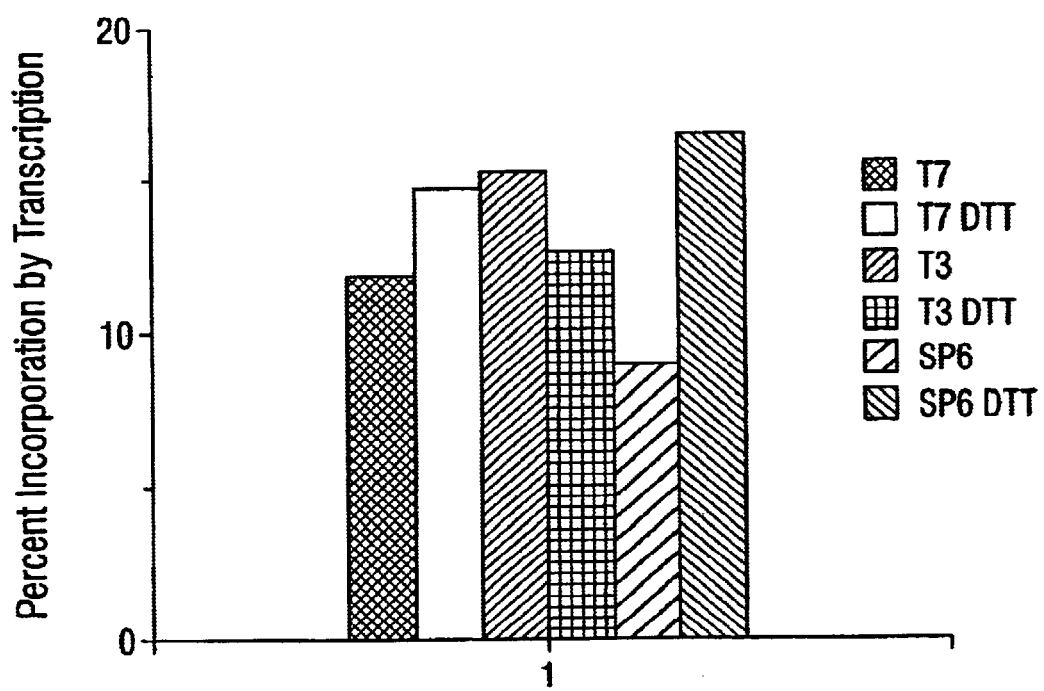
FIG. 3. DTT does not inhibit T7, T3 and SP6 RNA polymerases. Transcriptions were performed with T7, T3 and SP6 RNA polymerase in the presence and absence of 20 mM DTT. For each RNA polymerase reaction, pTRI-Xef DNA was the template and UTP[$\alpha^{32}$P] was included to measure the efficiency of transcription. Duplicates were performed for each reaction. TCA precipitations were performed on each transcription reaction to measure the percent of the UTP[$\alpha^{32}$P] incorporated into RNA.

The transcription reactions were based on the MAXIscript™ transcription kit (Ambion, Inc.). The following were assembled with or without 20 mM reducing reagent in a final volume of 18 μl: NTPs (0.5 mM each), 1 μg linearized DNA template, 2 μl 10×transcription buffer, and 0.2 μl UTP [α-$^{32}$P] (800 Ci/mmol). The reaction mixtures were incubated 60° C. for 10 minutes and then 2 μl of the either SP6, T7 or T3 RNA polymerase (10 units/μl) were added to the reactions, incubated 30° C. for 60 minutes and then TCA precipitated to assess the incorporation of the radioactive label. None of the three polymerases were inhibited by DTT (FIG. 3) or by DTE or β-mercaptoethanol.

2. Reducing Reagents and Heat Selectively Inactivate RNases but not DNase I.

DNase I is commonly used to degrade contaminating DNA in RNA preparations. To test whether the inactivation method affected DNase I activity, DNase I (final concentration of 0.4 units/µl) was added to water containing 20 mM DTT, DTE or β-mercaptoethanol. The mixture was incubated at 60° C. for 20 minutes. After the heat treatment, the DNase I activity was tested by incubating the treated DNase I with plasmid DNA (0.2 µg/µl) at 37° C. for one hour followed by electrophoresis in a 1% agarose gel. The DNA was completely degraded demonstrating that the activity of the treated DNase I was not affected by the reducing/heat treatment.

EXAMPLE 6

RNase Inactivation is Time Dependent

Figure 4:
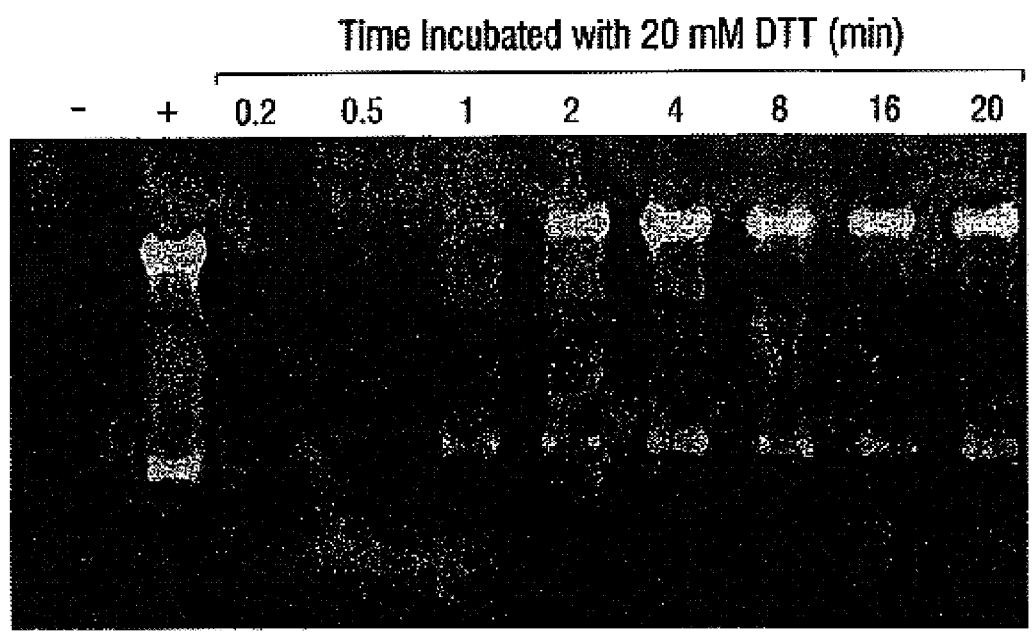
FIG. 4. Time dependence of RNase inactivation. The RNase mixture was made to 200 ng/ml in 1 mM sodium citrate (pH 6.4) in the presence of 20 mM DTT. 5 μl aliquots of the RNase mixture was heated for increasing amounts of time at 60° C. After heating, 4 μl (1 μg/μl) of total mouse brain RNA was added to each of the samples and incubated at 37° C. for 1 h. The samples were then fractionated on a formaldehyde denaturing 1% agarose gel in the presence of ethidium bromide. The RNA was detected by UV fluorescence. The lane labeled with the (+) is the mouse RNA substrate which was not subjected to any RNase. The lane labeled with the (−) is the mouse RNA substrate which was subjected to the RNase and 20 mM DTT without any heating.

The RNase mixture (200 ng/ml) was prepared in 1 mM sodium citrate (pH 6.4) with 20 mM DTT, followed by heating at 60° C. for 10 seconds, 30 seconds, 1 minute, 2 minutes, 4 minutes, 8 minutes, 16 minutes and 20 minutes. RNase activity was tested using the non-isotopic assay. Incubation for less than 30 seconds did not inactivate the ribonuclease mixture (FIG. 4). Treatment at 60° C. for 1, 2, and 4 minutes inactivated approximately 50%, 80% and 100% of the activity, respectively. Therefore, inactivation of RNase at 200 ng/ml by 20 mM DTT requires a 60° C. incubation for at least 4 minutes. Inactivation at a higher temperature such as 60° C. is preferred over 37° C. because the RNase mixture is inactive at the higher temperature. At 37° C., some of the RNA may be degraded by the RNase before the RNase is completely inactivated.

EXAMPLE 7

Sequential Inactivation of RNases by DTT Coupled with Heating

To perform sequential inactivation of RNases, 20 mM DTT was added to 1 mM sodium citrate buffer (pH 6.4). The RNase mixture was added to the buffer to final concentration of 200 ng/ml. Inactivation was carried out by heating the mixture at 60° C. for 20 minutes. To a portion of the heated RNase, additional RNase mixture was added to 200 ng/ml and followed by heating at 60° C. for 20 minutes. Three sequential additions of ribonuclease mixture and inactivation were performed. A negative control was set up for each sequential addition of ribonuclease mixture to the buffer but without reheating. RNase activity was measured non-isotopically. Sequentially added RNases (200 ng/ml) subjected to heating at 60° C. were completely inactivated. In contrast, sequentially added RNases to the same buffer which were not subjected to the 60° C. incubation caused complete RNA degradation, demonstrating that heating is required for RNase inactivation.

The sequential inactivations of the RNase mixture was possible because there was no detectable loss of DTT reducing power with each heating step, as measured below by the DTNB assay and therefore, a great excess of reduced DTT was still available to effect the inactivation of additional RNase.

To assess the effect that the ribonuclease mixture has on the oxidation of DTT, the RNase mixture at 1 µg/ml was incubated with DTT at 0.05, 0.1, 0.15, 0.2 and 0.25 mM at 60° C. for 20 minutes. 0.1 ml of each sample was added to 0.8 ml of 0.1 M $KPO_4$ (pH 7.7) and 0.1 ml DTNB in 0.1 KPO4 (pH 7.7). Samples which were not treated with heat were also subjected to the DTNB assay for comparison. The DTNB reaction mixtures were incubated at 21° C. for 10 minutes to allow the yellow color to develop. Absorbances were measured at 412 nm. The results were that there was no difference in the reactivity of the DTT whether it had been used to inactivate the RNase mixture or not. The results showed that there was no difference between the DTT used to inactivate the RNase mixture and non-reacted DTT.

EXAMPLE 8

DTT/Heat Inactivation of Ribonucleases is Stable

The RNase mixture was added to a final concentration of 200 ng/ml with 20 mM DTT to different solutions [water, TE (pH 8.0), 20×SSC, 10 ×MOPS, 1 M Tris (pH 8.0), 1 M Tris (pH 7.0), 1 mM sodium citrate (pH 6.4), 0.5 M EDTA (pH 8.0), 5×transcription buffer, 10×transcription buffer, 1×blocking buffer, 10×reverse transcription buffer, DNA/RNA hybridization buffer, in situ hybridization buffer, 1 M $MgCl_2$, 3 M sodium acetate, and formalin tissue fixative] followed by heating at 60° C. for 20 minutes to inactivate RNases. RNase activity was measured non-isotopically and isotopically.

The DTT-heating procedure inactivated RNase activity in all of buffers and solutions tested. Solutions containing the inactivated RNases were stored at 4° C. for one month and the RNase activity was then retested. Even after one month, none of the solutions had detectable RNase activity, indicating that the inactivation procedure is stable. Most of the solutions which were not treated with DTT and heat still had detectable RNase activity.

EXAMPLE 9

Oxidized DTT cannot Inactivate the RNase Mixture

Figure 5:
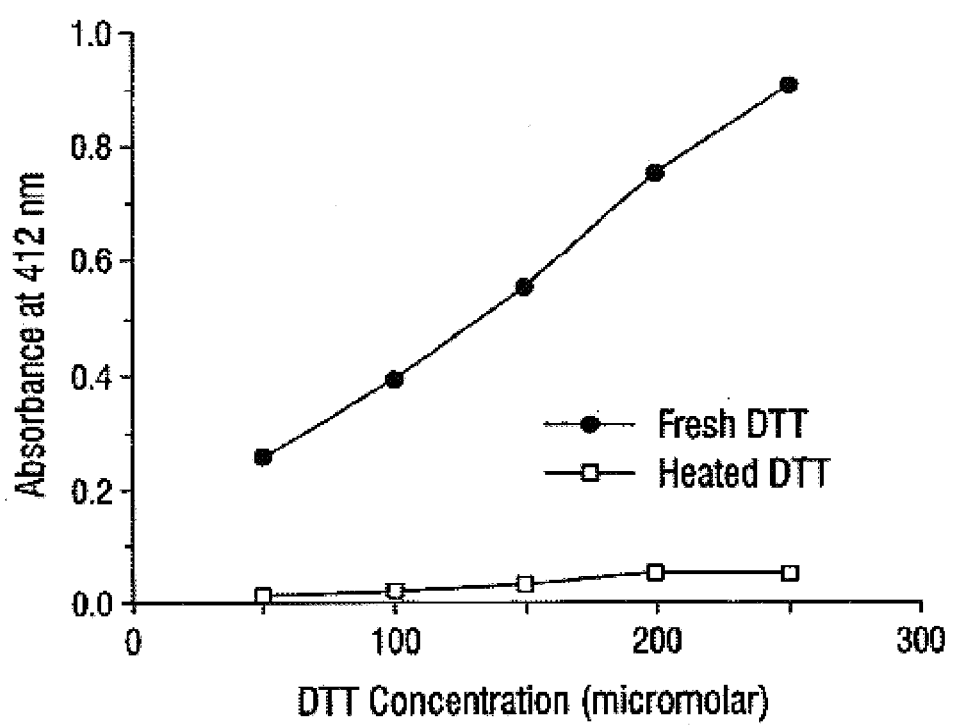
FIG. 5. DTT is oxidized by incubating at 65° C. for 6 days. DTT was made to 100 mM in water and incubated at 65° C. for 6 days. Fresh DTT and the heated 100 mM were diluted in water to different concentrations and subjected to the DTNB test. Absorbance at 412 nm indicates the reducing strength of the DTT.

DTT was made to 100 mM in water and incubated at 65° C. for 6 days. This material was diluted to 50, 100, 150, 200, 250 micromolar in water and then assayed for its reducing strength using the DTNB test described in Example 7 and compared to the same concentrations of DTT made fresh in water. The absorbance at 412 nm directly correlates with reducing strength. The greater the absorbance, the greater the reducing power. The DTT incubated at 65° C. was completely oxidized (FIG. 5).

The DTT incubated at 65° C. for 6 days was then tested for its ability to inactivate the RNase mixture. The heated DTT was diluted to 20 mM in the presence of the RNase mixture at 200 ng/ml in water and incubated at 60° C. for 20 minutes. RNase activity was measured using the non-isotopic assay. The oxidized DTT did not inactivate the RNase mixture.

EXAMPLE 10

Inactivation of an Unknown RNase in Alkaline Phosphatase Storage Solution

A commercial solution of unknown composition to the inventors designed to stabilize the storage of alkaline phosphatase was detected to have RNase activity using the isotopic assay. DTT was added to the alkaline phosphatase storage solution to final concentrations of 0, 2, 5, 10 and 20 mM and then incubated at 60° C. for 20 minutes. In the presence of 10 and 20 mM DTT, the alkaline phosphatase storage solution developed a precipitate and was not tested for RNase activity. The alkaline phosphatase storage solution treated with 0, 2 and 5 mM DTT and untreated alkaline phosphatase storage solution were tested for RNase activity using the isotopic assay. The alkaline phosphatase storage solution incubated at 60° C. in the presence of 2 and 5 mM DTT had no detectable RNase activity while the other two samples had similar levels of RNase activity. Thus, incubating the alkaline phosphatase storage solution at 60° C. without DTT was not sufficient to inactivate the unknown RNase. This experiment demonstrates that the RNase inactivation procedure is effective on unknown RNase contaminants.

EXAMPLE 11

Inactivation of an Unknown RNase in Psoralen Biotin

The Millennium™ Markers (Ambion, Inc.) are a set of RNA size markers from 0.5 to 9 kb in length. They are used for determining the length of an unknown RNA. These markers were being labeled with biotin using a psoralen biotin labeling procedure so that they could be detected non-isotopically on a nylon membrane. However, if the Millennium™ Markers were incubated at 37° C. for 16 hours after labeling with the psoralen biotin, they were degraded. The psoralen biotin was contaminated with an unknown RNase since the unlabeled Millennium™ Markers remained intact after the 37° C., 16 hour incubation. However, if the psoralen biotin labeled Millennium™ Markers were incubated at 90° C. for 10 minutes in the presence of 5 mM DTT after the labeling procedure to inactivate the RNase activity, then the labeled Millennium™ Markers remained intact after incubation at 37° C. for 16 hours.

EXAMPLE 12

Inactivation of Ribonucleases from a Crude Cellular Extract to Protect the Full Length Cellular RNA from Degradation The reduction-heating process may be used to generate a crude RNase free preparation of total RNA or polyA+ RNA from cells grown in tissue culture suitable for several different RNA analyses.

Cells grown in tissue culture are pelleted in a microfuge tube and the growth medium is removed. The cells are placed on ice. An isotonic solution such as phosphate buffered saline (PBS) containing 20 mM DTT is added to the cells to resuspend them. The cell suspension is quickly heated to between 60° C. and 90° C. for 10 to 20 minutes. The heating step would have two functions: 1) It denatures the cell membrane, releasing the cells' RNA and other contents into the PBS, and 2) It inactivates the RNases, thus preventing the degradation of the RNA. After heating, the cell suspension is centrifuged at high speed to pellet insoluble debris.

DNase I may be added to the cell suspension after the heat inactivation of the RNases. The contents would be incubated at 37° C. for 15 minutes to digest the cellular DNA. Finally, EDTA is added to 2 mM and contents incubated at 65° C. for 10 minutes to inactivate the DNase I. The cell suspension should now be suitable for RT-PCR.

It may be necessary to perform the initial heat inactivation at a higher temperature to achieve minimal RNA degradation. This process may also be performed on prokaryotic cells. It will be important to have a fast ramp time for the initial heat inactivation to minimize the time during which the temperature will be optimal for RNase activity.

EXAMPLE 13

Cysteine can be used to Heat Inactivate the RNase Mixture.

The RNase mixture was made to 200 ng/ml in 1 mM sodium citrate (pH 6.4) at 10, 20, 40 and 60 mM cysteine. The samples were incubated at 68° C. for 20 minutes. Total mouse RNA substrate was added to the samples and incubated for 37° C. for 1 hour, fractionated on a formaldehyde 1% agarose gel and detected by UV fluorescence. All of the RNase samples treated with cysteine and heat were inactivated.

EXAMPLE 14

DTT and Heat can be used to Enhance to Preservative Activity of RNAlater™

The term "RNAlater™" is a trademark of Ambion, Inc., for certain commercial formulations of the RNA preservation media. This technology is described in detail in U.S. Pat. application Ser. No. 09/127,435, filed Jul. 31, 1998, now U.S. Pat. No. 6,204,375, entitled "METHODS AND REAGENTS FOR PRESERVING RNA IN CELL AND TISSUE SAMPLES," which is incorporated herein by reference. This reagent functions by rapidly infiltrating cells with a high concentration of ammonium sulfate, causing a mass precipitation of cellular proteins. Importantly, cellular structure remains intact. The advantage of this is that cells can be preserved and still identified histologically. RNAlater™ inhibits RNase activity in tissues and thereby maintain full length RNA. Sample tissues are dropped in RNAlater™ solution. The RNA will remain intact for 1 day if kept at 37° C., intact for 1 week if kept at 21° C., and indefinitely at 4° C. The RNA may be preserved for longer periods at the higher temperatures if the ribonucleases in the tissues were more fully inactivated.

A reducing agent such as DTT or cysteine may be added to the RNAlater™ solution to 20 mM. When a tissue is added to the RNAlater™/DTT solution it would be heated to 40 to 600° C. for 10 to 20 minutes, thereby inactivating the RNases by reduction. In this manner, the advantages of both solutions may be realized with the result being even better assurance of protection from RNases.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aliaga, et al., "Isolation and Characterization of Polyribosomes from The Salivary Glands of Rhynchosciara Americana," Cell Differentiation, 4:243–255, 1975.

Allewell and Sama, "The Effect of Ammonium Sulfate on the Activity of Ribonuclease A", Biochem. Biophys. Acta, 341:484–488, 1974.

Barnard, "Ribonucleases," Annu. Rev. Biochem., 38:677–732, 1969.

Blackburn et al., "Ribonuclease Inhibitor from Human Placenta: Purification and Properties," J. Biol. Chem. 252:5904–5910, 1977.

Blumberg, "Creating a Ribonuclease-Free Environment," Methods Enzymol., 152:20–24, 1987.

Boshes, "Characterization of Two Populations by Cell Fractionation and Isotopic Labeling the Nucleic Acid and Protein Precursors," J. Cell Biol., 48:477–490, 1970.

Chirgwin, et al., "Isolation of Biologically Active Ribonucleic Acid from Sources Enriched in Ribonuclease," Biochemistry, 18:5294–5299, 1979.

Chomczynski and Sacchi, "Single Step Method of RNA Isolation by Acid Guanidine Isothiocyanate-Phenol-Chloroform Extraction," Anal. Biochem., 162:156–159, 1987.

Chomczynski, "Solubolization in Formamide Protects RNA from Degradation", Nucleic Acids Res., 20:3791, 1992.

Cleland, "Dithiothreitol, a New Protective Reagent for SH Groups," Biochemistry, 3:480–482, 1964.

Jacoli and Ronald, "Inhibition of Ribonuclease Activity by Bentonite," Can. J. Biochem., 51: 1558–1565, 1973.

Jones, "On the Efficacy of Commonly Used Ribonuclease Inhibitors," 69:469474, 1976.

Lin, "Inactivation of Pancreatic Ribonuclease with Hydroxylamine-Oxygen-Curric Ion," Biochimica et Biophysica Acta, 263:680–682, 1972.

Mendelsohn and Young, "Efficacy of Sodium Dodecyl Sulfate, Diethyl Pyrocarbonate, Proteinase K and Heparin Using a Sensitive Ribonuclease Assay," Biochimica et Biophysica Acta, 519:461–473, 1978.

Murphy et al., "A Potent, Cost-Effective RNase Inhibitor", Biotechniques, 18: 1068–1073, 1995.

Ryle and Anfinsen, "Studies on the Disulfide Bridges in Ribonuclease," Biochimica et Biophysica Acta, 24:633–635, 1957.

Sambrook, et al., "Molecular Cloning, A Laboratory Manual," pp. 7.16–7.52, 1989.

Spackman et al., "The Disulfide Bonds of Ribonuclease," J. Biol. Chem., 235: 648–659, 1960.

Wolf et al., "A Mechanism of the Irreversible Inactivation of Bovine Pancreatic Ribonuclease by Diethylpyrocarbonate," Eur. J. Biochem., 13:519–525, 1970.

Wiener et al., "Inhibition of Ribonuclease by Diethyl Pyrocarbonate and Other Methods," Biochimica et Biophysica Acta, 259:378–385, 1972.

Wu, et al., "Methods in Gene Biotechnology," CRC Press, Boca Raton, FL, pp. 29–56, 1997.

Zahler and Cleland, "A Specific and Sensitive Assay for Disulfides," J. Biol. Chem., 243:716–719, 1968.

Zale and Klibanov, "Why Does Ribonuclease Irreversibly Inactivated at High Temperature?," Biochemistry, 25:5432–5444, 1986.

What is claimed is:

1. A method of treating a sample to prepare an admixture with no detectable RNase A, RNase 1, and/or RNase T1 activity comprising:
   (a) obtaining a sample;
   (b) obtaining a thiol-containing reducing agent;
   (c) admixing the sample and the thiol-containing reducing agent to prepare an admixture; and
   (d) heating the admixture to a temperature and for a time required to result in the inactivation of any of RNase A, RNase 1, and/or RNase T1 present in the admixture;
   wherein there is no detectable RNase A, RNase 1, or RNase T1 activity in the admixture after the heating step.

2. The method of claim 1, further comprising treating a sample containing detectable RNase A, RNase 1, and/or RNase T1 activity prior to treatment.

3. The method of claim 2, wherein the detectable activity is RNase A activity.

4. The method of claim 2, wherein the detectable activity is RNase 1 activity.

5. The method of claim 2, wherein the detectable activity is RNase T1 activity.

6. The method of claim 1, further comprising treating a sample containing detectable RNase A, RNase 1, and RNase T1 activity prior to treatment.

7. The method of claim 1, wherein said thiol-based reducing agent is dithiothreitol (DTT), β-mercaptoethanol, dithioerythritol (DTE), or cysteine.

8. The method of claim 1, wherein the final concentration of the thiol-based reducing agent is between 1 and 200 mM in the admixture.

9. The method of claim 7, wherein said reducing agent is dithiothreitol (DTT).

10. The method of claim 9, wherein the final concentration of dithiothreitol (DTT) is between 1 and 200 mM in the admixture.

11. The method of claim 7, wherein said reducing agent is β-mercaptoethanol.

12. The method of claim 11, wherein the final concentration of β-mercaptoethanol is between 1 and 200 mM in the admixture.

13. The method of claim 7, wherein said reducing agent is cysteine.

14. The method of claim 13, wherein the final concentration of cysteine is between 1 and 200 mM in the admixture.

15. The method of claim 1, further comprising mixing the thiol-based reducing agent with a buffer prior to admixing in step (c).

16. The method of claim 15, wherein said buffer further comprises a chelator.

17. The method of claim 16, wherein the chelator is sodium citrate, ethylenebis(oxyethylenenitrilo)tetraacetic acid (EGTA), or ethylenediamine tetraacetic acid (EDTA).

18. The method of claim 1, wherein the admixture is heated to at least 37° C.

19. The method of claim 1, wherein the admixture is heated to at least 60° C.

20. The method of claim 1, wherein the mixture is heated for at least four minutes.

21. The method of claim 1, wherein the sample contains RNA.

22. The method of claim 21, wherein the sample contains purified RNA.

23. The method of claim 21, wherein the sample is a crude cell preparation.

24. The method of claim 21, wherein the sample is a cell sample.

25. The method of claim 21, further comprising performing a reverse transcriptase-polymerase chain reaction procedure with the admixture after the heating step.

26. The method of claim 1, wherein the sample comprises water, or further comprises Tris/EDTA (TE) buffer, NaCl/sodium citrate buffer (SSC), MOPS/sodium acetate/EDTA buffer (MOPS), Tris buffer, aqueous ethylenediamine tetraacetic acid (EDTA), nucleic acid hybridization buffer, sodium acetate buffer, formalin tissue fixative solution, in situ hybridization buffer, or nucleic acid storage buffer/solution.

27. The method of claim 1, further comprising conducting a second heating of the admixture for a temperature and for a time wherein there is no detectable RNase A, RNase 1, and/or RNase T1 activity present in the admixture after the second heating.

28. A method of treating an RNA sample to prepare an RNA-containing admixture with no detectable RNase A, RNase 1, and/or RNase T1 activity comprising:
 (a) obtaining an RNA sample;
 (b) obtaining a thiol-containing reducing agent;
 (c) admixing the sample and the thiol-containing reducing agent to prepare an admixture; and
 (d) heating the admixture to a temperature and for a time required to result in the inactivation of any of RNase A, RNase 1, and/or RNase T1 present in the admixture; wherein there is no detectable RNase A, RNase 1, or RNase T1 activity in the admixture after the heating step.

29. The method of claim 28, wherein the sample contains purified RNA.

30. The method of claim 28, wherein the sample is a crude cell preparation.

31. The method of claim 28, wherein the sample is a cell sample.

32. The method of claim 28, further comprising performing a reverse transcriptase-polymerase chain reaction procedure with the admixture after the heating step.

33. The method of claim 28, wherein said thiol-based reducing agent is dithiothreitol (DTT), β-mercaptoethanol, dithioerythritol DTE), or cysteine.

34. The method of claim 28, wherein the final concentration of the thiol-based reducing agent is between 1 and 200 mM in the admixture.

35. The method of claim 28, wherein the admixture is heated to at least 37° C.

36. The method of claim 28, wherein the admixture is heated at least 60° C.

37. The method of claim 28, wherein the mixture is heated for at least four minutes.

38. The method of claim 28, wherein said RNA sample contains detectable RNase A, RNase 1, and/or RNase T1 activity prior to treatment.

* * * * *

UNITED STATES PATENT AND TRADEMARK OFFICE
CERTIFICATE OF CORRECTION

PATENT NO. : 6,777,210 B1
DATED : August 17, 2004
INVENTOR(S) : Brittan L. Pasloske and William Wu It is certified that error appears in the above-identified patent and that said Letters Patent is hereby corrected as shown below:

Title page,
Item [54], Title, please delete "RNASE I" and insert -- RNASE 1 -- therefor.

Column 18,
Line 8, please delete "dithioerythritol DTE)" and insert -- dithioerythritol (DTE) -- therefor.

Signed and Sealed this

Eighteenth Day of January, 2005

JON W. DUDAS
*Director of the United States Patent and Trademark Office*